(12) United States Patent
Månsson et al.

(10) Patent No.: US 6,479,283 B1
(45) Date of Patent: Nov. 12, 2002

(54) STIMULATION, CULTURE AND PRESERVATION OF PANCREATIC CELLS

(75) Inventors: Per Månsson, Sollentuna; Tomas Lundin, Enköping; Christer Busch, Tromsø, all of (SE)

(73) Assignee: Ascendia AB, Sollentuna (SE)

( * ) Notice: Subject to any disclaimer, the term of this patent is extended or adjusted under 35 U.S.C. 154(b) by 0 days.

(21) Appl. No.: 09/381,650

(22) PCT Filed: Mar. 16, 1998

(86) PCT No.: PCT/SE98/00475
§ 371 (c)(1),
(2), (4) Date: Dec. 17, 1999

(87) PCT Pub. No.: WO98/41617
PCT Pub. Date: Sep. 24, 1998

(30) Foreign Application Priority Data

Mar. 18, 1997 (SE) .............................................. 9700983

(51) Int. Cl.[7] .................................................. C12N 5/00
(52) U.S. Cl. ........................ 435/325; 435/366; 435/404
(58) Field of Search ................................. 435/325, 366, 435/404, 405

(56) References Cited

U.S. PATENT DOCUMENTS

| | | | |
|---|---|---|---|
| 4,038,139 A | * | 7/1977 | Birch |
| 4,104,124 A | * | 8/1978 | Srinivasan et al. |
| 4,330,622 A | * | 5/1982 | Desai |
| 5,013,714 A | * | 5/1991 | Lindstrom et al. |
| 5,641,647 A | * | 6/1997 | Fischer et al. |

* cited by examiner

Primary Examiner—Leon B. Lankford, Jr.
(74) Attorney, Agent, or Firm—Heller Ehrman White & McAuliffe LLP

(57) ABSTRACT

A method for stimulating pancreatic cells to synthesize and/or excrete insulin comprises contacting insulin-producing cells, in particular their aqueous suspension, with a water-soluble cellulose derivative, in particular selected from alkylated, hydroxyalkylated, and alkylated-hydroxyalkylated cellulose or a mixture thereof. A medium for the culture of pancreatic β-cells contains an effective cell-stimulating amount of a cellulose derivative. It can be used to stimulate pancreatic β-cells to produce and/or excrete insulin. An apparatus for such stimulation comprises a container holding a solution of a cellulose derivative in an aqueous culture medium. Stimulation of pancreatic β-cells by a cellulose derivative is useful in the management of diabetes. Further preservative or therapeutic methods using the aqueous cellulose derivatives are disclosed.

Figure 1:
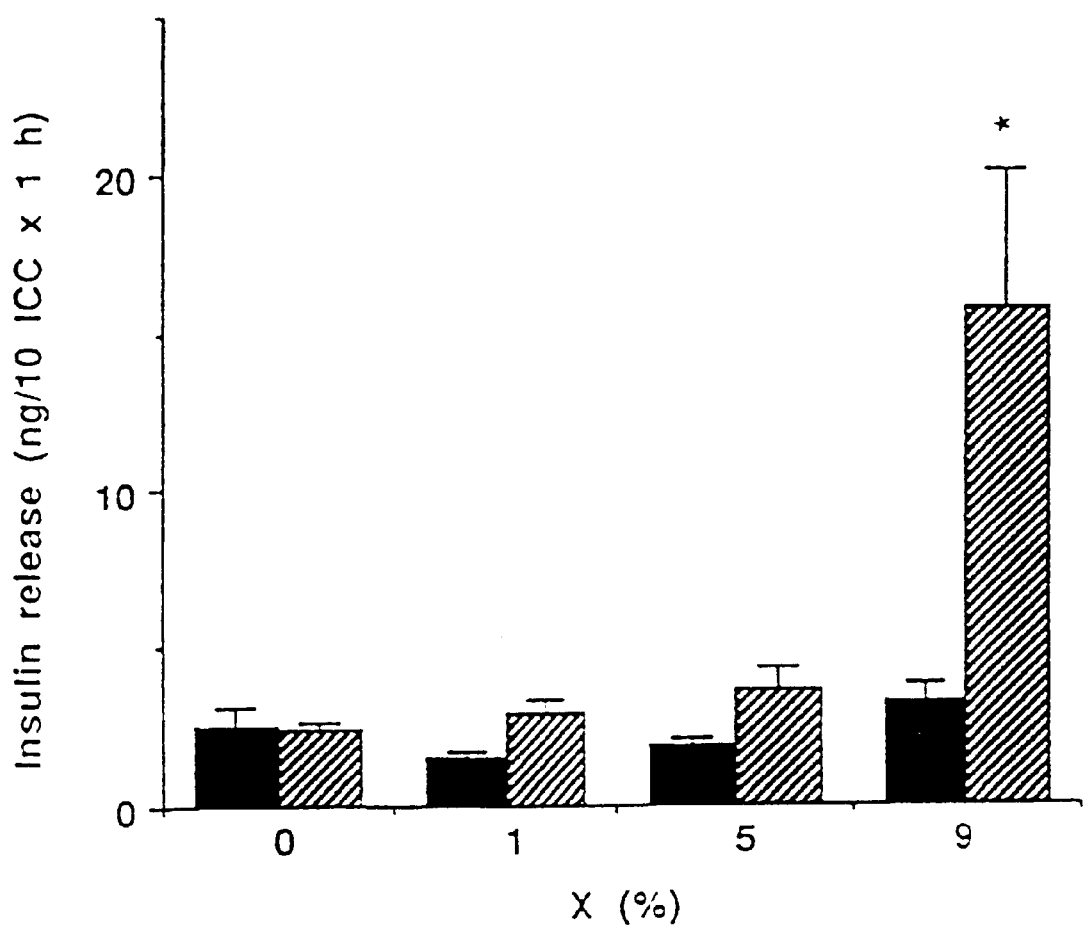

16 Claims, 7 Drawing Sheets

STIMULATION, CULTURE AND PRESERVATION OF PANCREATIC CELLS

FIELD OF THE INVENTION

The present invention relates to a method for the stimulation of pancreatic cells to produce and/or excrete insulin, the stimulation being provided in connection with culture, transport, storage, isolation, transplantation and similar. The pancreatic cells considered herein include mature insulin-producing β-cells and their precursors, fetal β-cells.

The present invention also relates to a method for in-vitro cultivation of human adult and/or fetal cells, in particular cell types considered difficult or impossible to cultivate in existing media, such as stem cells, fibroblasts, neural cells and epithelial cells.

The present invention also relates to a method for in-vitro cultivation of human adult and fetal cells, a method for the expression of peptides in bacteria, in particular E. coli, a method for wound healing, a method for skin treatment, and a method for preservation and/or transport and/or storage of tissue and organ transplants.

Furthermore the present invention relates to a means for carrying out said methods and to uses of the means.

BACKGROUND OF THE INVENTION

Transplantation of insulin-producing pancreatic cells is an attractive alternative to the presently used life-long administration of insulin to diabetics whose pancreas does not produce this vital hormone or only does produces it in insufficient amounts. At present pancreatic transplantation means transplantation of the entire organ or a major part thereof. The transplantation of pancreatic islets only, that is, cell clusters comprising β-cells, is considered to be in an early experimental state. Transplantation of pancreatic islets only should be more attractive than transplantation of the entire pancreas since the availability of such organs of human origin is limited. The preparation of viable porcine or human islets for clinical investigation is known (Gray D W R et al., *Diabetes* 1984, 33:1055; Ricordi C et al., *Diabetes* 1990, 37:1377) and such implantation has provided encouraging results (for instance, Scharp D W et al., *Diabetes* 1990, 39:515). The remaining problem, however, is how to provide sufficient amounts of these cell preparations, and how to stimulate them to excrete substantial amounts of insulin. For various reasons it has been proposed to use fetal pancreatic tissue (for a survey, se: Andersson A and Sandler S., *Transplantation Reviews* 6 (1992) 20–38; reference to this survey also comprises reference to research papers cited therein).

It is believed (cf. Andersson and Sandler, op. cit.) that successful transplantation of fetal pancreatic tissue requires the explanted tissue to be kept in culture for some time before implantation. In addition to the tissue being kept in a viable state it is desirable to stimulate it for β-cell growth and differentiation to promote excretion of insulin.

A method known in the art for preparation of fetal tissue particles (ICC, islet-like transplantation of pancreatic islets cell clusters containing β-cells) comprises degradation of fetal pancreatic tissue with collagenase (cf. Andersson and Sandler, op. cit.). For various reasons comparatively low differentiated tissue is used for their preparation resulting in preparations containing few cells that immunochemically stain for insulin, and thus are identified as insulin-producing. On the other hand ICC have full potential for later differentiation at proper culture conditions. Such differentiation is considered, i.a., to be stimulated by human growth hormone, prolactin, and inhibitors of poly(ADP-ribose) synthetase, such as nicotine amide. In addition, the excretion of insulin itself can be stimulated. By nature D-glucose is the foremost stimulating agent but cell response in vitro to D-glucose can be low or nil, in particular with low-differentiated pancreatic tissue. Other agents, however, for instance inhibitors of phospho-diesterase, such as theophylline, stimulate the excretion of insulin at high glucose levels.

OBJECTS OF THE INVENTION

It is thus an object of the invention provide a method for the stimulation of insulin-producing β-cells isolated from fetal or mature pancreatic tissue to produce and/or excrete insulin, the definition "insulin-producing" cells also including cells competent for insulin production upon stimulation and/or differentiation, to keep such cells in a viable condition, to cultivate such cells, and to store and transport such cells. Another object of the invention is to provide a means for carrying out said method. Other objects of the invention are uses for such cells being stimulated, kept in a viable condition, transported or stored. A further object of the invention is an apparatus to be used in connection with cell stimulation, transport, storage or cultivation.

Further objects of the invention will become apparent from the study of the following summary of the invention, the description of preferred embodiments thereof, and of the appended claims.

SUMMARY OF THE INVENTION

In accordance with the present invention there is provided a method of the aforementioned kind comprising contacting insulin producing cells, in particular an aqueous suspension of insulin-producing cells, with a water-soluble cellulose derivative when being stimulated or stored, transported or cultured in preparation of stimulation. Such preparation of stimulation includes the preparation for transplantation. Preferred cellulose derivatives are alkylated, hydroxyalkylated, and alkylated/hydroxyalkylated celluloses. Examples for such cellulose derivatives are hydroxyethyl cellulose, hydroxypropyl cellulose, methyl cellulose, ethyl cellulose, hydroxyethyl-methyl cellulose, hydroxyethyl-ethyl cellulose, hydroxypropyl-methyl cellulose. Most preferred is hydroxypropyl-methyl cellulose (HPMC). Aqueous solutions (true or colloidal) of the cellulose derivatives according to the invention are known to be viscous. The term cellulose derivative as used herein excludes derivatives of cellulose obtained by substantial degradation of the cellulose chain to fragments having a weight average molecular weight of 2,000 or less. The term cellulose derivative as used herein comprises pharmaceutically acceptable derivatives of cellulose obtained by substitution of hydrogen in cellulose hydroxyl groups by alkyl groups, preferably by $C_1$–$C_5$ alkyl groups.

Non-cellulose based carbohydrate polymers, such as alginates or agar (EP-A 363 125) or hyaluronic acid do not exert the substantial β-cell stimulating effect according to the invention though providing aqueous solutions of substantial viscosity.

The aqueous solution of the cellulose derivative according to the invention can also contain other agents, such as nutrients in form of salts, amino acids, peptides, proteins, hormones or similar. Cell culture media of various kind can be provided with appropriate amounts of the cellulose derivative according to the invention whereby an aqueous β-cell stimulating solution according to the invention is obtained.

In accordance with the invention are further disclosed uses for a β-cell stimulating aqueous solution containing said cellulose derivative. These uses are preferably selected from culture, transport, transplantation, and storage of pancreatic cells.

In accordance with the invention there is also provided an apparatus for carrying out said method, the apparatus comprising a container for β-cells containing an aqueous solution of the cellulose derivative according to the invention.

According to a second aspect of the present invention is disclosed a method for in-vitro cultivation of human adult and/or fetal cells, in particular cells considered difficult or impossible to cultivate in existing media, such as stem cells, neural cells, fibroblasts and skin cells, the method comprising contacting said cells being held in culture with a water-soluble cellulose derivative. Preferred cellulose derivatives are alkylated, hydroxy-alkylated, and alkylated/hydroxy-alkylated celluloses. Examples for such cellulose derivatives are hydroxyethyl cellulose, hydroxypropyl cellulose, methyl cellulose, ethyl cellulose, hydroxyethyl-methyl cellulose, hydroxyethyl-ethyl cellulose, hydroxypropyl-methyl cellulose. Most preferred is hydroxypropyl-methyl cellulose (HPMC).

According to a third aspect of the present invention is disclosed a method for the expression of peptides in bacteria, in particular *E. coli*, the method comprising contacting said bacteria with a water-soluble cellulose derivative. Preferred cellulose derivatives and examples thereof are given in the preceding paragraph.

According to a fourth aspect of the present invention is disclosed a method for wound healing, the method comprising contacting the wound with a water-soluble cellulose derivative. Preferred cellulose derivatives and examples thereof are given above.

According to a fifth aspect of the present invention is disclosed a method for dermal treatment aiming at the preservation of skin integrity and regeneration, the method comprising contacting the skin with a water-soluble cellulose derivative. Preferred cellulose derivatives and examples thereof are given above.

According to a sixth aspect of the present invention is disclosed a method for the expression of plasmids in bacteria, in particular *E. coli*, the method comprising contacting said bacteria when held in culture with a water-soluble cellulose derivative.

According to a seventh aspect of the present invention is disclosed a method for the preservation and/or transport and/or storage of tissue and organ transplants, the method comprising contacting the transplant with a preservation and/or transport and/or storage effective amount of a water soluble cellulose derivative.

According to an eight aspect of the present invention is disclosed a method for promoting the healing of the respiratory tract epithelium including that of the larynx, trachea, bronchi and pulmonary epithelium, the method comprising administration of a therapeutically effective amount of a water-soluble cellulose derivative in form of microdroplets of its aqueous solution provided, for instance, by a nebulizer.

Contacting with a water soluble cellulose derivative includes contacting with an aqueous solution of the derivative.

According to a ninth aspect of the invention is disclosed a method for in-vitro stimulation of eucaryotic cells being held in culture, said stimulation comprising accelerating cell maturation or excretion of metabolic products, the method comprising contacting said cells with a cell maturing or cell stimulating amount of a water-soluble cellulose derivative.

According to a tenth aspect of the invention is disclosed a method for in-vitro cultivation of eucaryotic cells being held in culture, the method comprising contacting said cells with a water-soluble cellulose derivative.

The means according to the invention for carrying out the aforementioned methods comprises a water soluble cellulose derivative. Preferred water soluble cellulose derivatives are alkylated, hydroxy-alkylated, and alkylated/hydroxy-alkylated celluloses. Examples for such cellulose derivatives are hydroxyethyl cellulose, hydroxypropyl cellulose, methyl cellulose, ethyl cellulose, hydroxyethyl-methyl cellulose, hydroxyethyl-ethyl cellulose, hydroxypropyl-methyl cellulose. Most preferred is hydroxypropyl-methyl cellulose (HPMC).

While not being bound by any hypothesis in regard of the beneficial effect of the water-soluble cellulose derivative of the invention, this effect on living cells, cell aggregates, tissues, and organs for transplantation is thought to be due to the aqueous solution of the cellulose derivative providing an environment which is more natural—more structured—than the aqueous environment provided by known culture media.

Further advantageous and preferred features of the invention are disclosed in the appended claims and the following description of preferred embodiments of the invention, said non-limitative embodiments however only being provided for illustrative purposes.

PREFERRED EMBODIMENTS OF THE INVENTION

Figure 2:
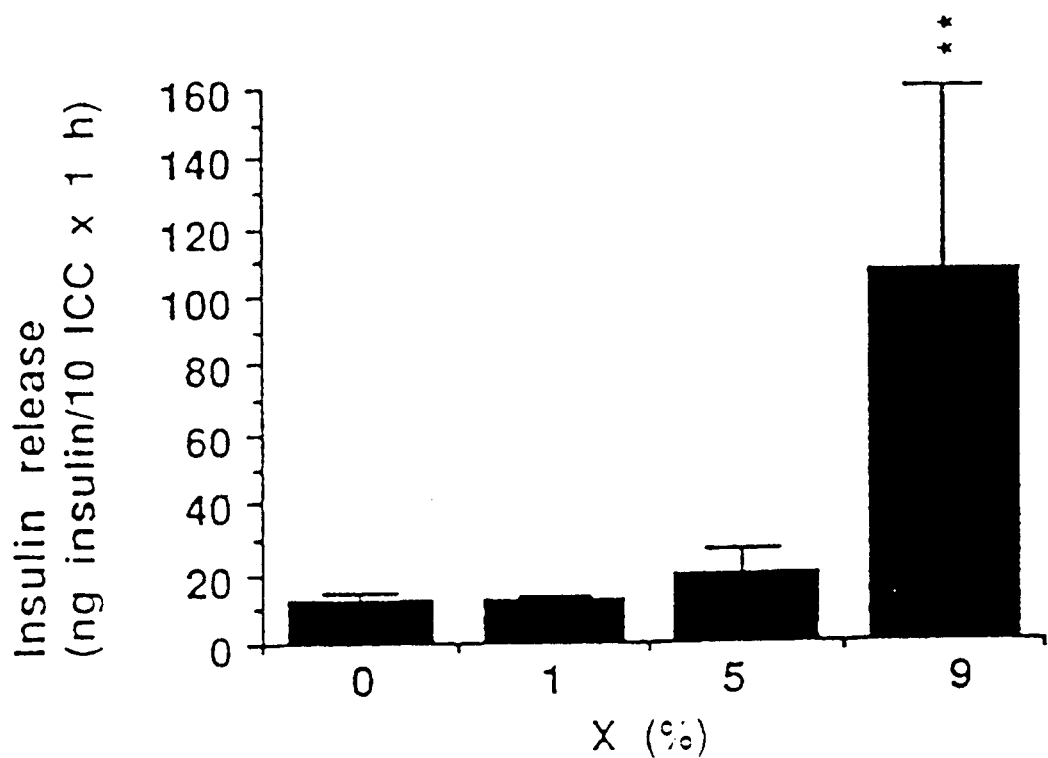
Figure 3:
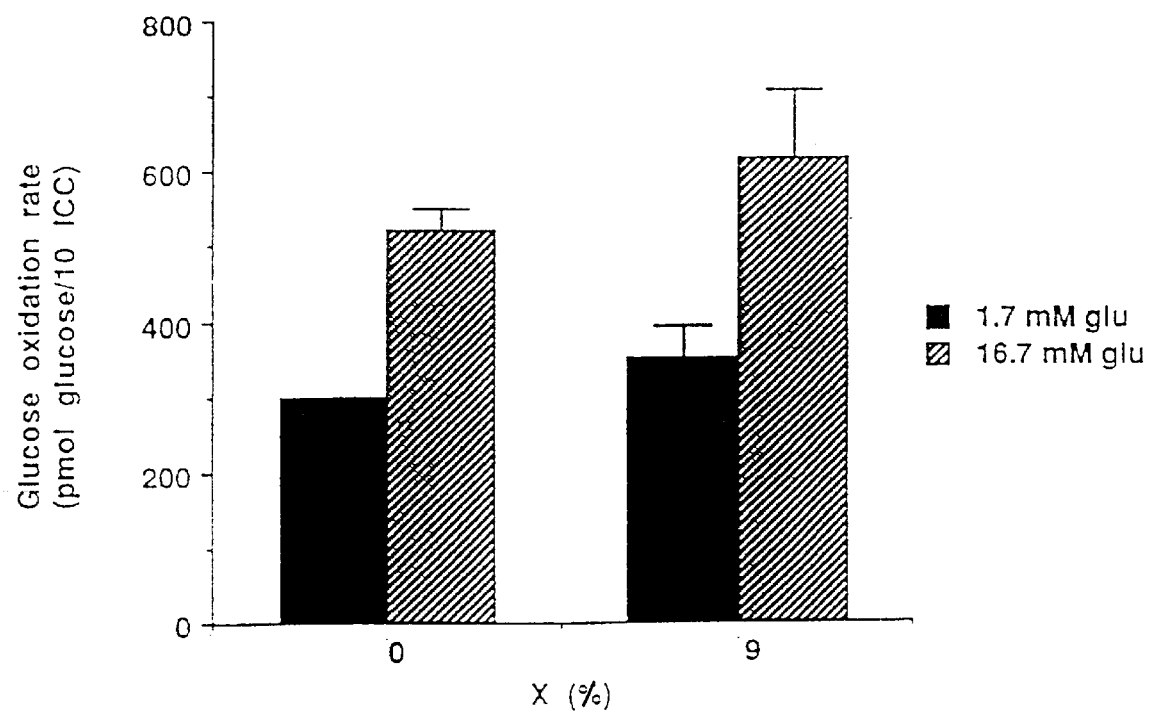
Figure 4:
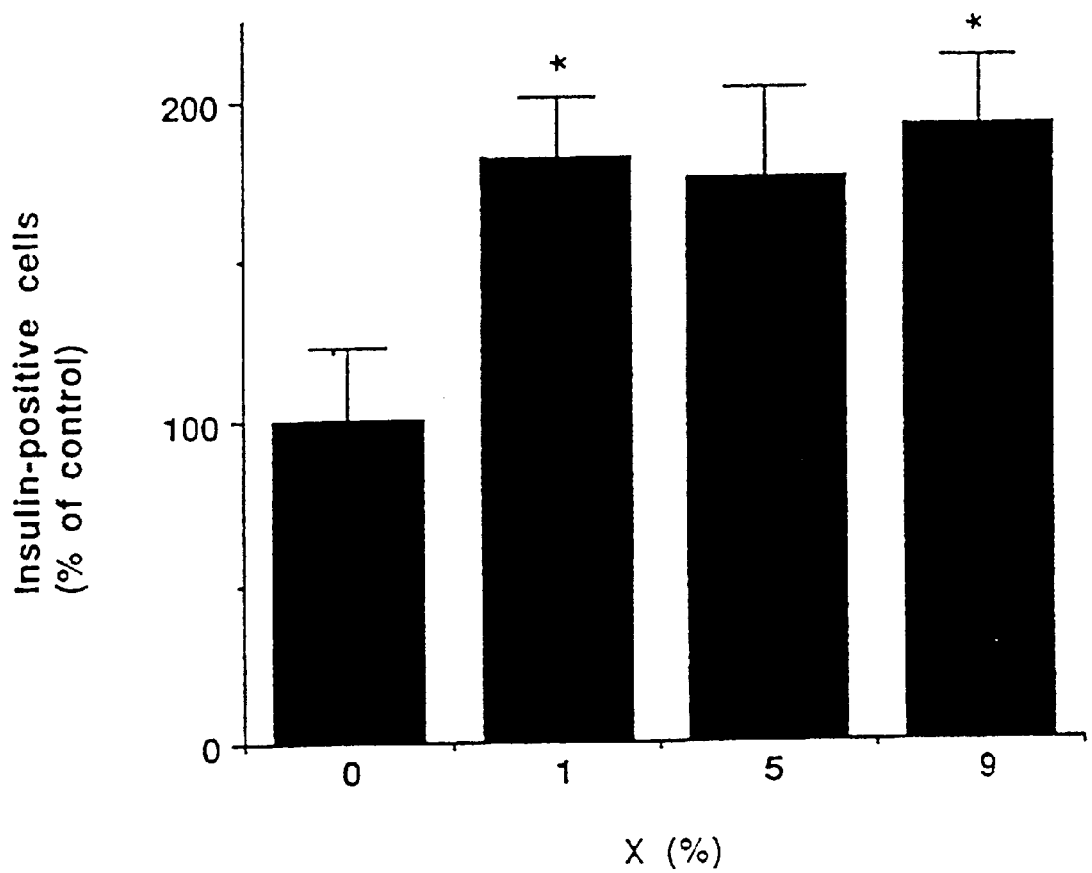
Figure 5:
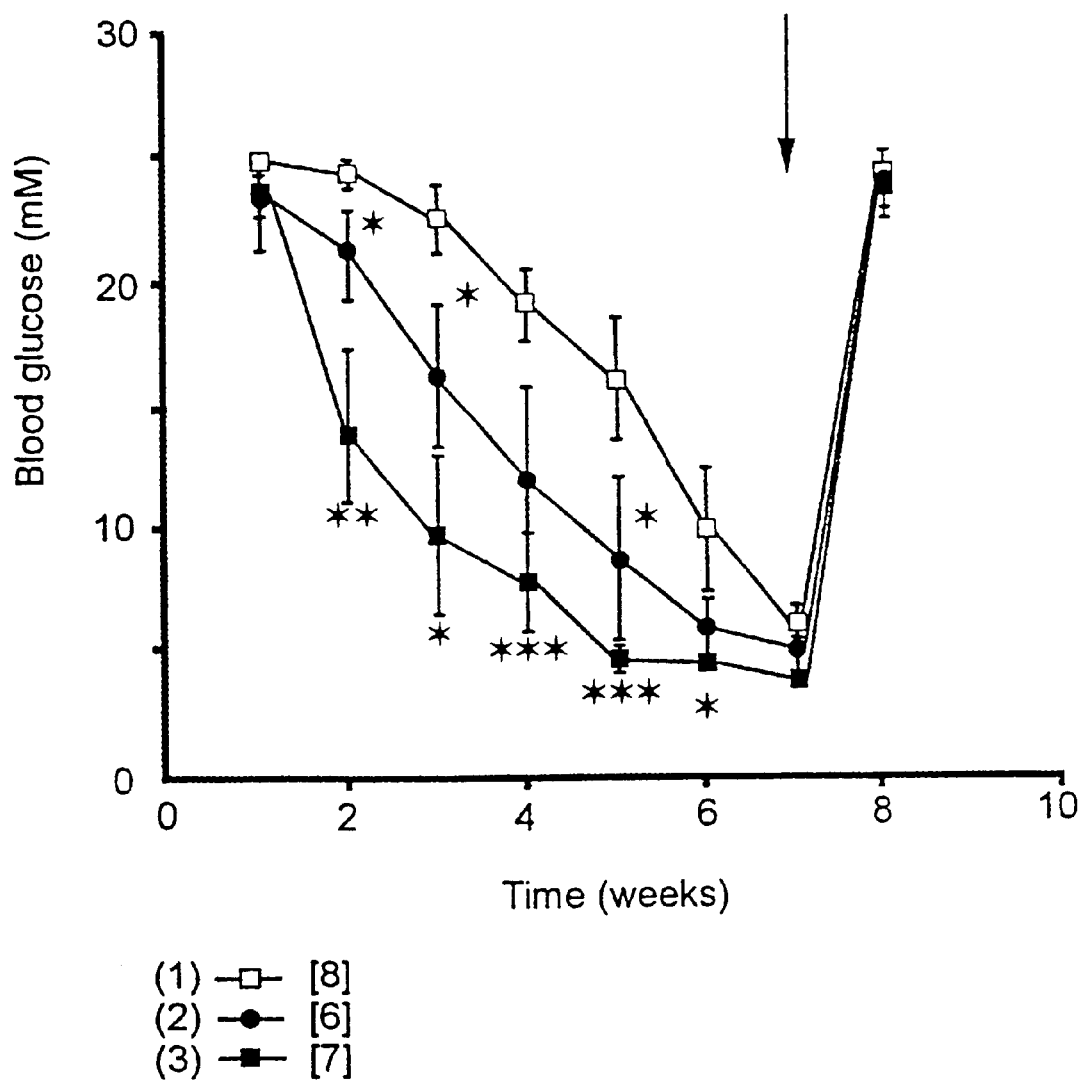
Figure 6:
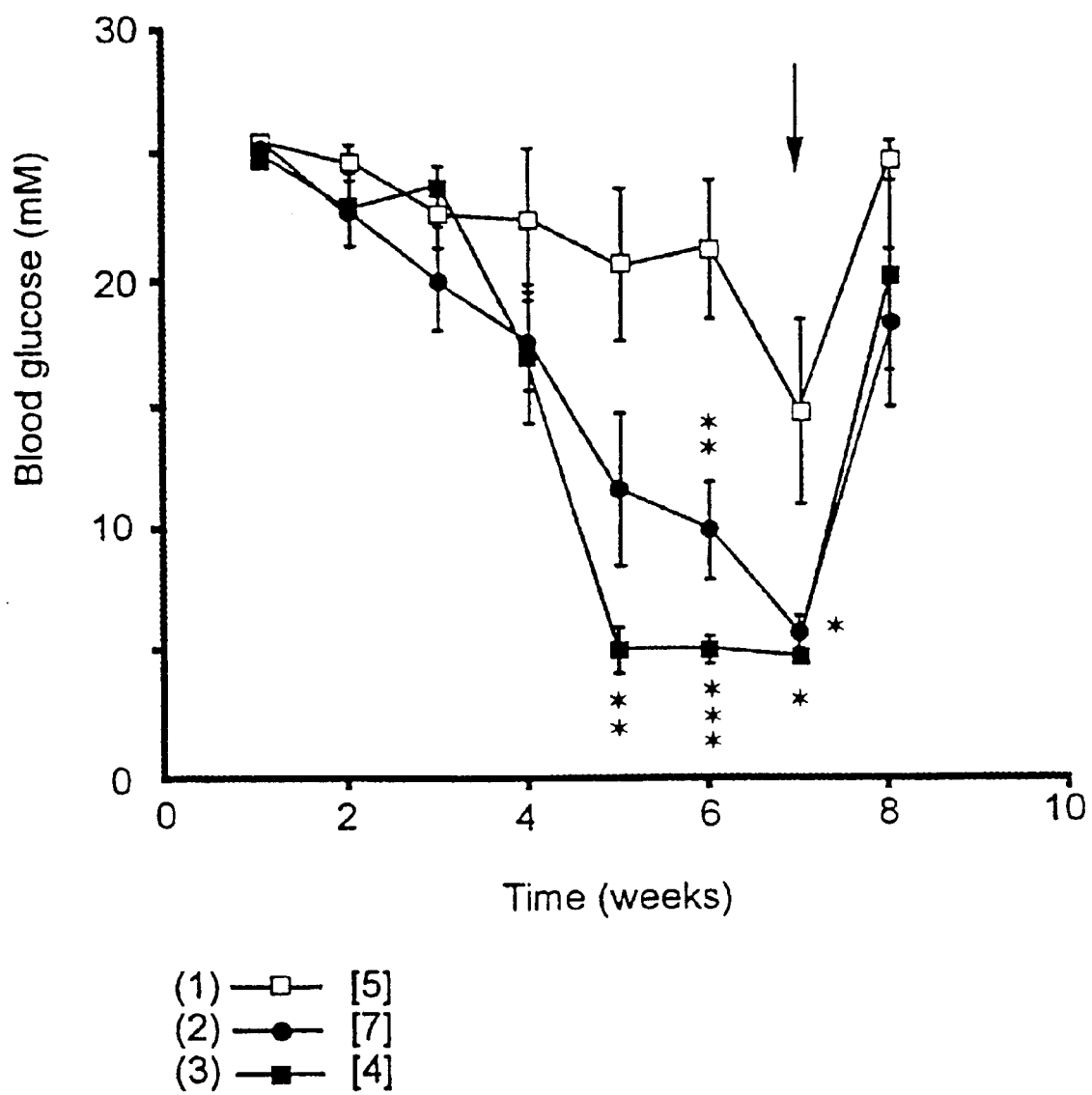
Figure 7:
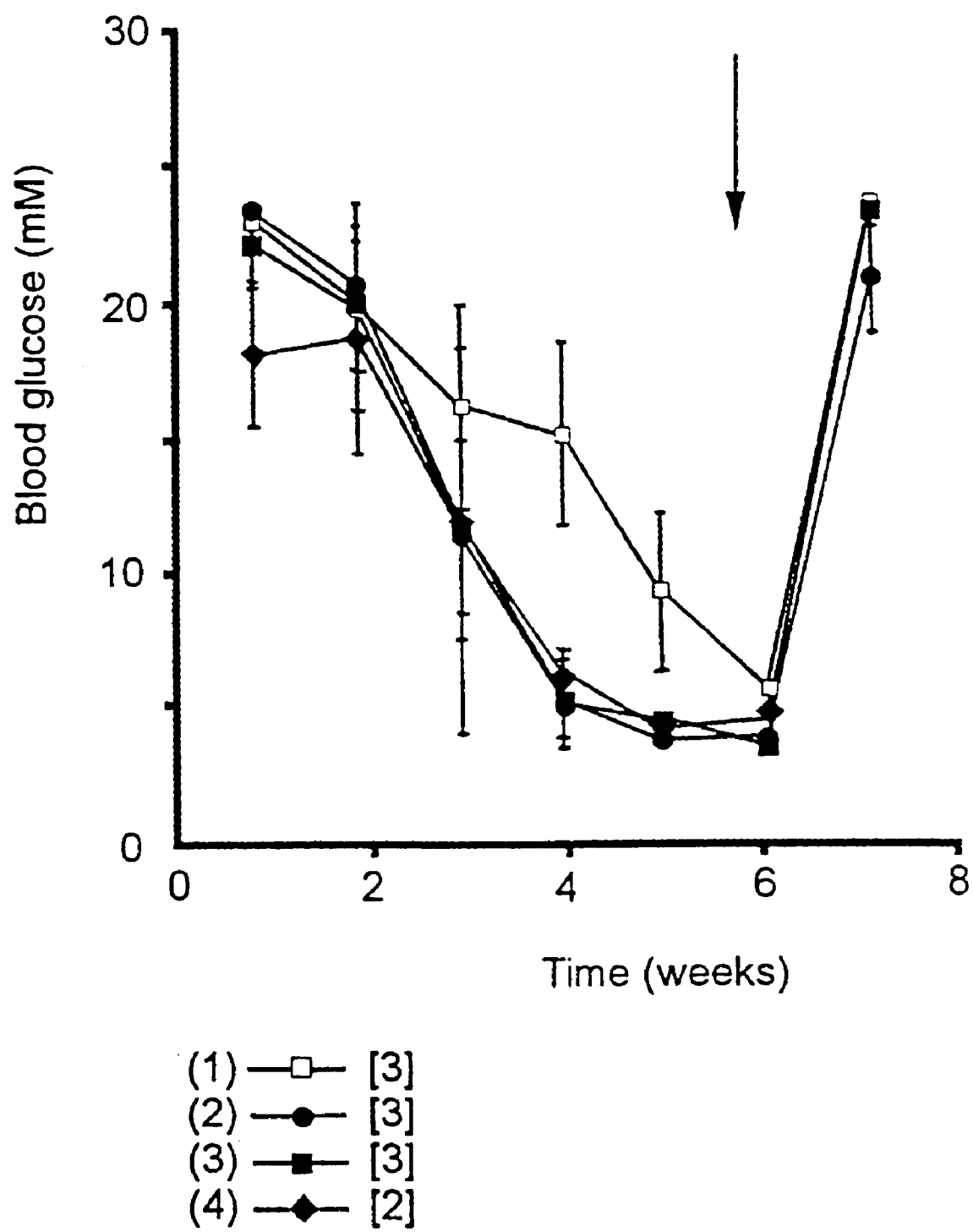

The drawing pertaining to said preferred embodiments comprises a number of figures illustrating, in form of diagrams:

FIG. 1 glucose-stimulated insulin release of fetal porcine ICC,

FIG. 2 stimulation of proinsulin and total protein biosynthesis of fetal porcine ICC, FIG. 3 the glucose oxidation rate of fetal porcine ICC, FIG. 4 the number of insulin-positive cells in fetal fetal porcine ICC, and FIGS. 5–7 transplantation of ICC in naked mice with induced diabetes.

EXAMPLE 1

Effects of HPMC on DNA and Insulin Content of Porcine Islet-like Cell Clusters (ICC)

Fetal porcine pancreatic explants had been cultured for five days in medium RPMI 1640 with addition of human serum and HPMC (hydroxypropylmethyl cellulose) as indicated in columns 1 and 2 of Table 1.

TABLE 1

| Culture condition | | DNA content (μg DNA/- 10 ICC) | Insulin content (ng insulin/- 10 ICC) (% of control) | Insulin/DNA (ng insulin/- μg DNA) (% of control) |
|---|---|---|---|---|
| Serum | HPMC | | | |
| 10 | 0 | 1.62 ± 0.12 | 58.1 ± 14.2 | 36.6 ± 10.5 |
| 9 | 1 | 1.61 ± 0.11 | 68.1 ± 15.8 | 40.9 ± 9.6 |
| | | | 136 ± 20.8 | 133 ± 19.5 |
| 5 | 5 | 1.73 ± 0.08 | 116 ± 33.5* | 68.0 ± 20.5 |
| | | | 198 ± 34.9* | 182 ± 29.3* |

TABLE 1-continued

| Culture condition | | DNA content ($\mu$g DNA/- 10 ICC) | Insulin content (ng insulin/- 10 ICC) | Insulin/DNA (ng insulin/- $\mu$g DNA) |
|---|---|---|---|---|
| Serum | HPMC | | (% of control) | (% of control) |
| 1 | 9 | 1.59 ± 0.11 | 164 ± 56.2 | 104 ± 35.6 |
| | | | 290 ± 63.1* | 292 ± 58.9* |

\* denotes P <0.05 vs the control group, using Student's paired t-test.

EXAMPLE 2
Effects of HPMC on Islet (Pro)insulin (PI) and Total Protein (TOT) Biosynthesis Rates of Porcine Islet-like Cell Clusters (ICC)

The ICC had been cultured as described in Table 1. Then they were incubated for 2 h in KRBH+2 mg/ml BSA in the presence of 16.7 mM glucose and 50 $\mu$Ci/ml of L-[4.5-$^3$H] leucine. Thereafter the ICC were homogenized and the (pro)insulin biosynthesis rate was measured by an immunoabsorption method; the total protein biosynthesis rate was measured after TCA-precipitation. Results are shown in Table 2. Values are means+SEM for 6–7 experiments.

TABLE 2

| Culture cond. | | | | PI/TOT × 100 |
|---|---|---|---|---|
| Serum (%) | HPMC (%) | PI | TOT | |
| | | (dpm × 10$^3$/10 islets × 2h) | | (%) |
| 10 | 0 | 5.1 ± 0.95 | 63 ± 15.7 | 3.0 ± 0.6 |
| 1 | 9 | 5.1 ± 2.4 | 165 ± 15.5 | 3.6 ± 1.3 |
| 5 | 5 | 6.4 ± 0.64 | 202 ± 17.6 | 3.7 ± 0.6 |
| 5 | 50 | 7.8 ± 1.0*** | 217 ± 16.3** | 3.7 ± 0.4* |

\* and ** denote P <0.05 and P <0.01, respectively, vs the control group (10% serum only), using Student's paired t-test.

EXAMPLE 3
Glucose-stimulated Insulin Release of Fetal Porcine Pancreatic Islet-like Cell Clusters (ICC)

Pancreatic explants had been cultured for five days in medium RPMI 1640 with addition of 10% human serum (HS) only, or 9% HS+1% X, or 5% HS+5% X, or 1% HS+9% X. ICC were subsequently harvested and incubated for 1 h at 37° C. ($O_2$:$CO_2$; 95:5) in a Krebs-Ringer bicarbonate buffer containing 10 mM Hepes, 2 mg/ml bovine serum albumin and 1.7 mM glucose (black bars) or 16.7 mm glucose (hatched bars). Insulin released to the medium was measured by radio-immunoassay. Results are shown in FIG. 1. Values are means+SEM for 8 experiments.

EXAMPLE 4
Theophylline-stimulated Insulin Release of Fetal Porcine Pancreatic Islet-like Cell Clusters (ICC)

The ICC had been cultured as described in Example 1 and were subsequently harvested and incubated for 1 h at 37° C. ($O_2$:$CO_2$; 95:5) in a Krebs-Ringer bicarbonate buffer containing 10 mm Hepes, 2 mg/ml bovine serum albumin and 16.7 mm glucose+5 mm theophylline. Results are shown in FIG. 2. Values are means+SEM for 8 experiments.

EXAMPLE 5
Glucose Oxidation Rate of Fetal Porcine Pancreatic Islet-LIKE Cell Clusters (ICC)

The ICC had been cultured as described in FIG. 1. The islets were incubated for 1 h at 37° C. ($O_2$:$CO_2$; 95:5) in a Krebs-Ringer bicarbonate buffer containing 10 mm Hepes and 1.7 mm (black bars) or 16.7 mm glucose in the presence of D-[U-$^{14}$C]glucose. Results are shown in FIG. 3. Values are means+SEM for 3 experiments.

EXAMPLE 6
Insulin-positive Cells in Fetal Porcine Pancreatic Islet-LIKE Cell Clusters (ICC)

The ICC had been cultured as described in Example 1. On day 5 the ICC were harvested, washed, fixed in 9% formalin, embedded in paraffin, and sections of 6 $\mu$m were cut. The sections were then immunocytochemically stained for insulin using a guinea pig anti-bovine insulin antibody. Results are shown in FIG. 4. Values are means+SEM for 4 experiments.

EXAMPLE 7
Transplantation in Naked Mice with Induced Diabetes

Diabetes was induced in naked mice by injection of alloxan (Dunn, J S, and McLetchie, Lancet 2 (1943) 384; Boquist L, Acta Pathol. Microbiol. Scand., Sect. A, 88 (1980) 201) resulting in hypoglycemia within a few days indicated by blood glucose levels >25 mm. After about one week intact ICCs from other mice of this strain were transplanted to the hypoglycemic anaesthetized animals. An incision was made in the abdominal wall and the left kidney was mobilized. A small hole was made in the kidney's thin cartilage capsule and a pipette containing ICC was carefully inserted therethrough under the capsule. The ICCs were deposited within the capsule, the pipette withdrawn and the abdominal wall and skin sutured.

In a first series of experiments an ICC standard dose of 2×3 $\mu$l corresponding to 600 ICC was injected. Three types of ICCs were compared:

(1) control, i.e. ICC islets cultured in medium RPMI 1640+10 mm nicotine amide+10% human serum (HS);

(2) ICC islets cultured in medium RPMI 1640+10 mm nicotine amide+10% human serum (HS)+9% of 1.5% HPMC in saline;

(3) ICC islets cultured in medium RPMI 1640+10 mm nicotine amide+10% human serum (HS)+9% of 1.5% HPMC in saline+1 mm 2-deoxyglucose (DG). The reason for incorporating was the finding that DG reduces fibroblast growth in these cultures and facilitates harvesting of ICCs. In contrast DG, as was shown by separate experiments, does not affect the differentiation of fetal porcine ICCs in respect of giving rise to glucose stimulated release of insulin.

Results of experiments (1)–(3) are shown in FIG. 5. Numbers in square brackets indicate number of animals. The animals were transplanted at time 0. Blood glucose was determined on day 7 and in weekly intervals thereafter. The arrow indicates nephrectomy, i.e., the kidney with ICC transplant was removed and blood glucose was determined one week thereafter. After nephrectomy blood glucose decreases more rapidly in animals of group (2) and (3) than of group (1) indicating the curative effect of the transplants in diabetes. Histologic examination of the removed transplants demonstrated their structural integrity comprising well integrated β-cells.

In a second series of experiments the amount of ICC was decreased to 1×3 $\mu$l ICC (FIG. 6). All other parameters were set as in the first series described above. The result was essentially the same as in the first series. The controls (1) were not cured of their diabetes within 7 weeks (a blood glucose level of 10 $\mu$M being considered as a cure threshold) while animals in groups (2) and (3) became normoglycemic. The use of DG seems to have a clearly beneficial effect on the reduction of blood glucose levels.

In a third series of experiments the ICC dosage was raised to 3×3 μl, in addition to groups (1)–(3) an additional group of animal (4) was added in which the HPMC solution was one in a neutral phosphate buffer instead of saline. The treatment provided in groups (2)–(4) was effective in decreasing blood glucose levels (FIG. 7). This series of experiments was however disturbed by the death of one animal in group (4).

What is claimed is:

1. A composition comprising:

pancreatic β-cells suspended in a water-soluble cellulose derivative dissolved in a cell culture medium or a physiologically compatible carrier solution, the medium or solution optionally further containing agents selected from the group consisting of salts, amino acids, peptides, proteins, and hormones.

2. The composition of claim 1, wherein the cellulose derivative is an alkylated cellulose, a hydroxyalkylated cellulose, an alkylated-hydroxyalkylated cellulose, or a mixture thereof.

3. The composition of claim 2, wherein the cellulose derivative is selected from hydroxyethyl cellulose, hydroxypropyl cellulose, methyl cellulose, ethyl cellulose, hydroxyethyl-methyl cellulose, hydroxyethyl-ethyl cellulose, and hydroxypropyl-methyl cellulose.

4. The composition of claim 3, wherein the cellulose derivative is hydroxypropyl-methyl cellulose.

5. The composition of claim 1 comprising:

pancreatic β-cells suspended in a water-soluble cellulose derivative dissolved in a cell culture medium, the medium optionally further containing agents selected from the group consisting of salts, amino acids, peptides, proteins, and hormones.

6. The composition of claim 5, wherein the cellulose derivative is an alkylated cellulose, a hydroxyalkylated cellulose, an alkylated-hydroxyalkylated cellulose, or a mixture thereof.

7. The composition of claim 6, wherein the cellulose derivative is selected from hydroxyethyl cellulose, hydroxypropyl cellulose, methyl cellulose, ethyl cellulose, hydroxyethyl-methyl cellulose, hydroxyethyl-ethyl cellulose, and hydroxypropyl-methyl cellulose.

8. The composition of claim 7, wherein the cellulose derivative is hydroxypropyl-methyl cellulose.

9. A method for stimulating pancreatic β-cells to produce and/or excrete insulin comprising contacting said cells with an effective amount of a water-soluble cellulose derivative dissolved in a cell culture medium or a physiologically compatible carrier solution, the medium or solution optionally further containing agents selected from the group consisting of salts, amino acids, peptides, proteins, and hormones.

10. The method of claim 9, wherein said stimulation is provided in culture and/or during transport, transplantation, or storage of said cells.

11. The method of claim 9, wherein the cellulose derivative is an alkylated cellulose, a hydroxyalkylated cellulose, an alkylated-hydroxyalkylated cellulose, or a mixture thereof.

12. The method of claim 11, wherein the cellulose derivative is selected from hydroxyethyl cellulose, hydroxypropyl cellulose, methyl cellulose, ethyl cellulose, hydroxyethyl-methyl cellulose, hydroxyethyl-ethyl cellulose, and hydroxypropyl-methyl cellulose.

13. The method of claim 12, wherein the cellulose derivative is hydroxypropyl-methyl cellulose.

14. The method of claim 11, wherein said stimulation is provided in culture and/or during transport, transplantation, or storage of pancreatic cells.

15. The method of claim 12, wherein said stimulation is provided in culture and/or during transport, transplantation, or storage of pancreatic cells.

16. The method of claim 13, wherein said stimulation is provided in culture and/or during transport, transplantation, or storage of pancreatic cells.

* * * * *